United States Patent [19]

Johnston

[11] Patent Number: 5,316,260

[45] Date of Patent: May 31, 1994

[54] OPHTHALMIC INSTRUMENT STAND

[76] Inventor: Jack L. Johnston, 4708 18th Ave. W., Bradenton, Fla. 34209

[21] Appl. No.: 962,867

[22] Filed: Oct. 19, 1992

[51] Int. Cl.$^5$ ............................................... A47F 1/14
[52] U.S. Cl. .................................. 248/648; 248/123.1
[58] Field of Search ............... 248/648, 123.1, 125, 248/362, 280.1, 162.1, 331, 121

[56] References Cited

U.S. PATENT DOCUMENTS

| | | | |
|---|---|---|---|
| 4,523,732 | 6/1985 | Biber et al. | 248/123.1 |
| 4,660,798 | 4/1987 | Kinoshita | 248/648 |
| 4,815,832 | 3/1989 | Nagano | 248/123.1 X |
| 5,143,333 | 9/1992 | Warden | 248/123.1 |

FOREIGN PATENT DOCUMENTS 2033796  5/1980  United Kingdom ............... 248/648

Primary Examiner—Ramon O. Ramirez

[57] ABSTRACT

A multi-jointed support arm accepting various Ophthalmic instruments and platforms is suspended by cables distributing the weight of said arm and instruments up and over two sets of pulleys and back down to a counterweight. A switch actuated electro-mechanical lock prevents accidental descent of the instrument platform support arm. Upward movement of the support arm is unrestricted. An outer shroud conceals mechanical components of this device prior to the support arm.

3 Claims, 3 Drawing Sheets

5,316,260

OPHTHALMIC INSTRUMENT STAND

BACKGROUND OF THE INVENTION

1. Field of the invention

The present invention relates in general to Ophthalmic instruments and equipment and in particular to Ophthalmic instrument support stands.

2. Prior art

In the examination of patients by Ophthalmologist, Optometrists, and other eye care professionals, there is a need to bring various instruments into position directly in line with the patient's field of vision and to move such instruments, upon completion of their role in a particular phase of examination, to a position that is out of the way of patient and examiner. Instruments of examination include but, are not limited to, slit lamps, the, tonometers, and refractometer. These instruments employ a high degree of precision in manufacture and use which makes them relatively heavy while requiring a very stable platform for accurate operation.

In the past, stands with counterbalanced arms for the delivery of instrument platforms have been devised. In these type devices, the practice has been to distribute the weight in a single suspension vertical configuration which requires a large, heavy base to prevent the stand from overturning when the support arm is extended while bearing the weight of an instrument. Such a configuration has set limits on the horizontal extension of these stands in a position directly beside the patient chair. This placement interferes with the necessary access to the area directly beside the patient during the course of examination.

Another restriction imposed by the generally vertical orientation of prior designs is a limit of downward vertical movement of the instrument support arm in such devices. Such restriction prohibits the examination of wheel chair bound patients without moving them from their chairs into the patient chair because of the lower sitting level of the wheelchair. Moving such patients is difficult and potentially dangerous for both patient and examiner.

Due to the mandatory lateral positioning of prior stands, the instrument support arm approaches the patient's legs in a perpendicular manner also limiting downward movement of the arm and allowing for the possibility of injury in accidental arm decent.

Prior designs also provide locking mechanisms which prevent upward as well as downward movement of the instrument support arm. Preventing upward movement allows for the possibility of trapping an unattended patient who may be unfamiliar with the operation of lock switches and instrument support arm operation.

SUMMARY OF THE INVENTION

The principal object of the invention is to provide a device for the storage and delivery of precision Ophthalmic instruments in a way that allows better across to both instrument and patient in a clinical eyecare setting.

It is also the object of the invention to provide a device allowing the safe examination of wheelchair bound patients.

Another object of the invention is to provide a device allowing a free upward movement of the instrument platform to prevent possible injury to patient and examiner.

The aforementioned objects can be accomplished by providing an Ophthalmic instrument stand having a relatively low base comprised of a frame of upright members supporting a multi-jointed arm whose free end engages various Ophthalmic instrument platforms and instruments; the weight of said instruments being supported through the use of a pair of cables which transmit the weight up and over a front pair of pulleys to and over a rear set of pulleys and, down to a counterweight.

The preferred embodiment of the present invention includes a closed top, hexagonal shroud over a base, having four vertical elements of equal length which form a frame for distributing weight in a horizontal as well as vertical manner, creating a lower overall profile than devices employing a strictly vertical distribution of weight. Each vertical member supports one of the four pulleys and are aligned in a rectangular pattern. The vertical members are connected at their upper ends by a frame which maintains their alignment. A fifth vertical element is situated between and slightly behind two vertical elements mentioned previously along the front short side of the rectangle. This fifth vertical member acts as a guide for the electro-mechanical un-locking device which is supported by a roller frame assembly. The roller frame assembly operates in a vertical manner between the previously mentioned vertical elements and is endowed with rollers which retain its position laterally. The roller frame assembly is suspended by cables which ascend to the pulleys at the upper end of the front vertical members then, to the pulleys at the upper end of the back vertical members and down to a counter weight. The roller frame assembly supports the instrument platform support arm which attaches to it's front face. The instrument platform support arm is comprised of a lower support, lower arm and upper arm. The lower support is attached to the roller frame assembly in a vertical orientation. The upper end of the lower support receives the lower support arm end at a 90 degree angle and allows the lower support arm to swivel 360 degrees. The free end of the lower support arm receives the end of the upper support arm which orients to the lower support arm in a parallel manner. The upper support arm swivels 360 degrees and its free end accepts various Ophthalmic instrument platforms. A single position switch is located on the top of the upper support arm and is connected via shielded wiring to the electro-mechanical servo un-locking mechanism. Depressing this switch frees the entire instrument platform support arm to move in a downward direction. Upward movement is possible at all times without activating the un-locking mechanism electrical service to various Ophthalmic instruments is provided by a receptacle at the free end of the upper support arm which is connected to shielded wiring routed through the support arm to the base.

DETAILED DESCRIPTION

Figure 1:
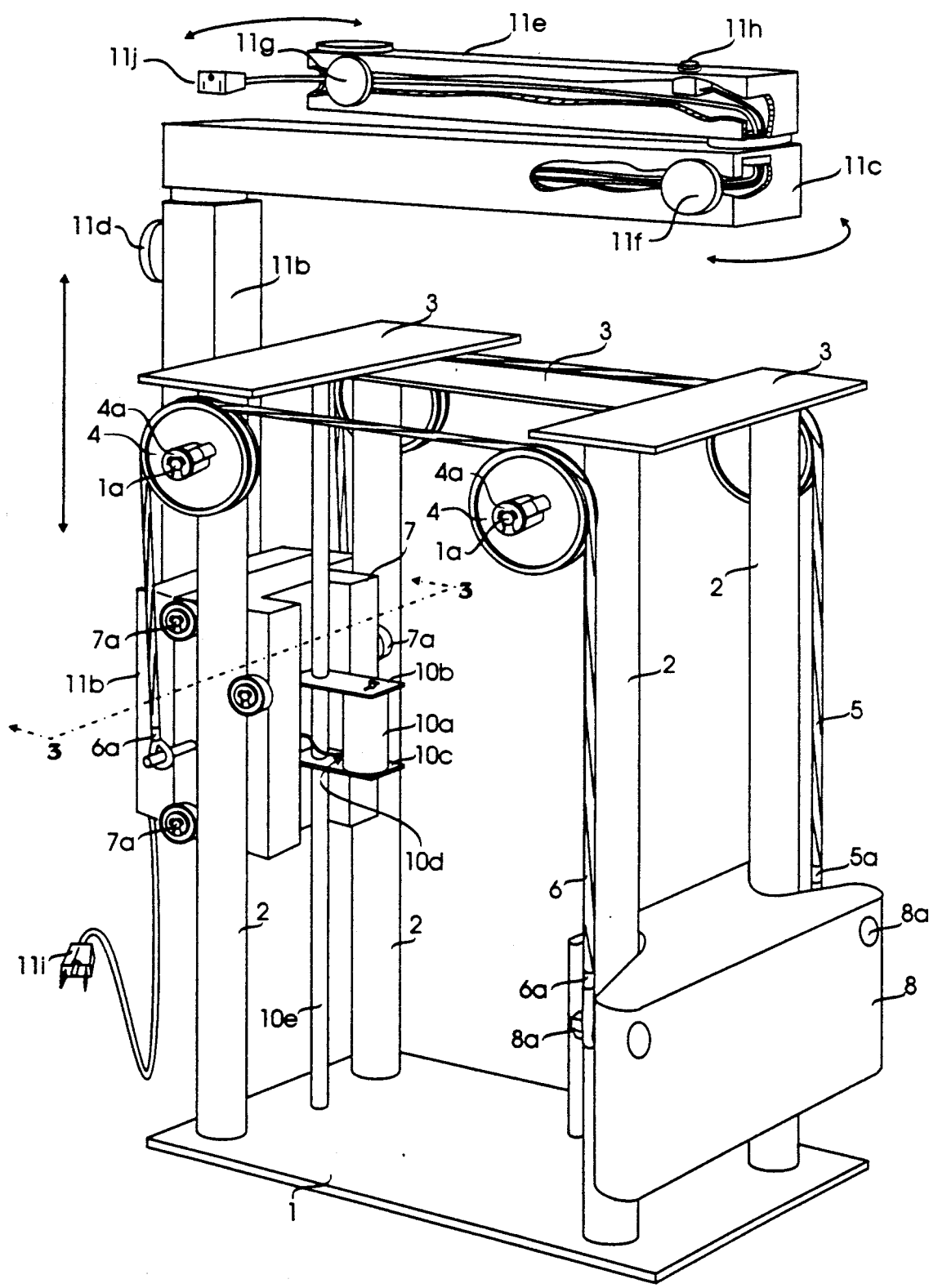
FIG. 1 is a perspective view of the Ophthalmic instrument stand in accordance with the present invention.
Figure 2:
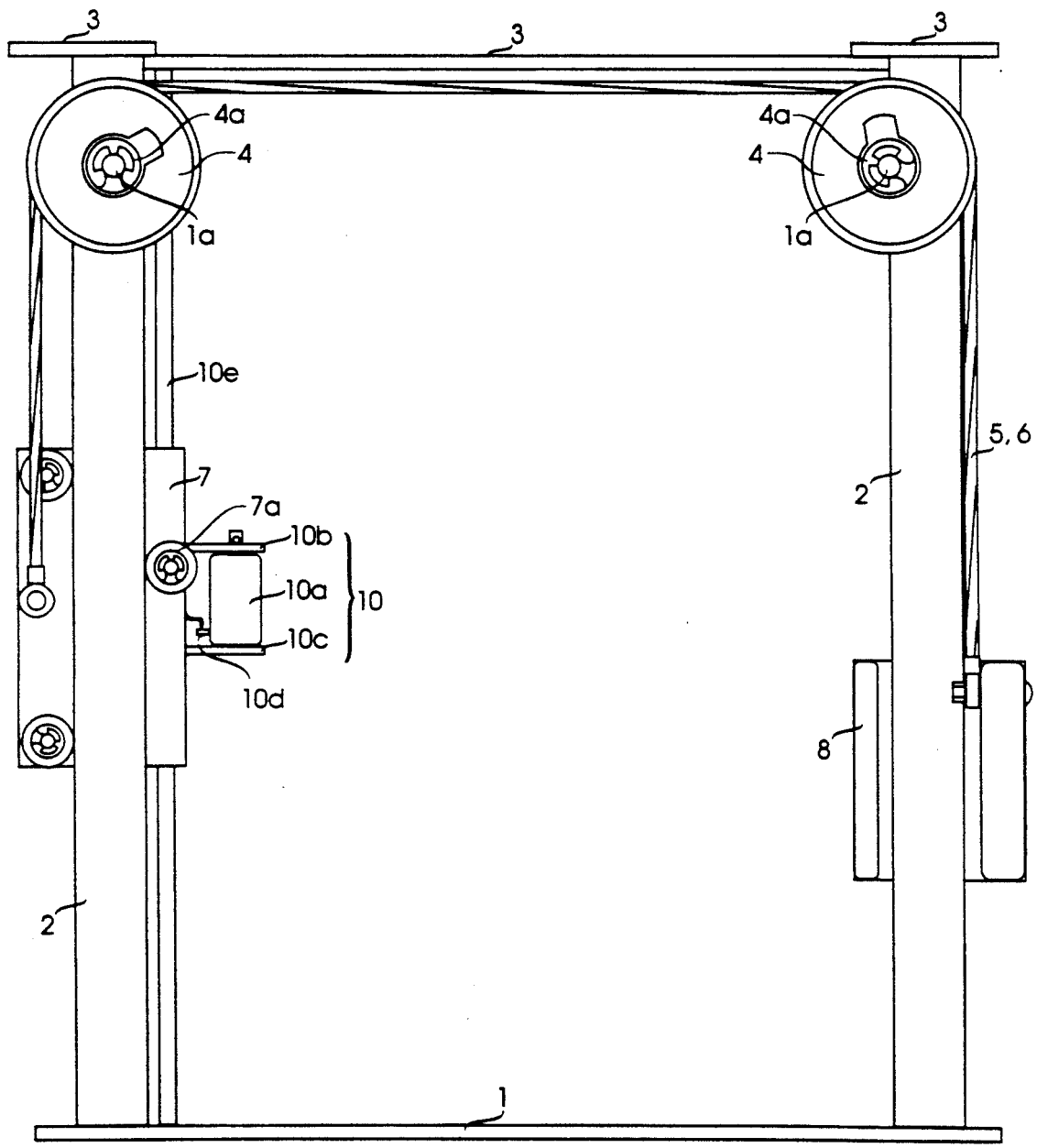
FIG. 2 is a side elevation of the invention without support arms, (11b, 11c, and 11e).
Figure 3:
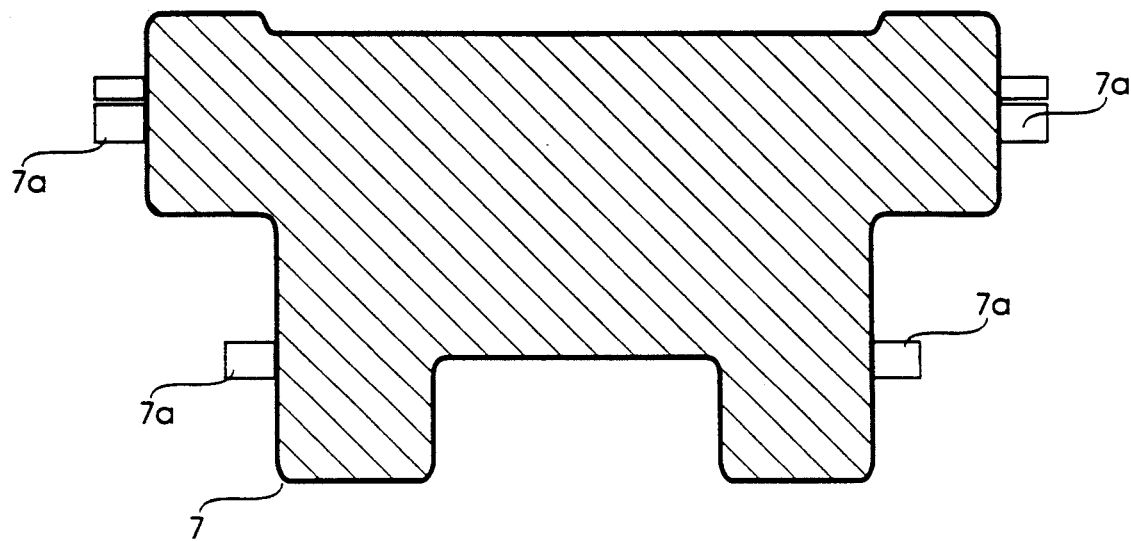
FIG. 3 is a lateral cross section of roller frame assembly (7) of FIG. 1.

As shown in the drawings, the preferred embodiment of the Ophthalmic instrument stand in accordance with the current invention includes a base (1) which is the ground engaging member supporting 2 front and 2 rear uprights (2) of equal length, which are preferably welded to the base (1) forming a rectangular pattern. The uppermost ends of the uprights are welded to a frame (3) forming a rigid and dimensionally stable support frame. Situated on the sides of the uprights (2) as to be perpendicular to the base are pulleys (4) on shafts, (1a) retained by clips (4a) as seen in FIGS. 1 and 2. Right cable (5) and left cable (6) transmit the load of roller frame assembly (7) up and over pulleys (4) at front, then over and down pulleys (4) at the rear to counter weight (8). Cables (5) and (6) are affixed to shafts (8a) by means of loops in cables formed by the formed by the attachment of clips (5a) and (6a). Cables (5) and (6) are similarly affixed to shafts on roller frame. Eccentric bearings (7a) are situated on shafts in roller frame assembly (7) as seen in FIGS. 1 and 2 and restrict roller frame assembly (7) movement laterally within the uprights (2). Attached to the rear of the roller frame assembly (7) is the un-locking mechanism assembly (10). This assembly is comprised of an electro mechanical servo (10a), locking shoe (10b), an electrical connection (10d), and servo mounting bracket (10c). The Front portion of the locking shoe (10b) pivots about guide rod (10e) which is situated between and slightly behind front uprights (2) and, is surrounded laterally by protrusions in the form of the roller frame assembly (7). Guide rod (10e) is attached to base (1) at its extreme lower end and to frame (3) at its extreme upper end. Action of the electromechanical servo (10a) results in the vertical movement of the rear part of locking shoe (10b) which angles the eccentric hole in the locking shoe's (10b) front portion which surrounds guide rod (10e), releasing the roller frame assembly (7). The orientation of the eccentric hole in locking shoe (10b) allows free upward movement of the roller frame assembly (11) is attached to the front of the roller frame assembly (7) by bolts (11a) through the lower end of lower support (11b). The upper end of lower support (11b) is tapped to receive the shaft of lower support arm (11c). Handwheel lock (11d) is located at the upper front of lower support (11b) and screws through the wall of same and against the shaft of lower support arm (11c) to provide a means of locking lower support arm (11b) forms a 90 degree angle. The shaft of upper support arm (11e) is received into a collar in lower support arm's (11c) free end. The upper support arm (11e) maintains a generally parallel orientation to the ground plane and rotates 360 degrees a handwheel lock (11f) locks the upper support arm (11e) at any point along this axis of rotation in a similar manner to handwheel lock (11d). The free end of upper support arm (11e) is tapped to receive the shafts of various Ophthalmic instrument platforms and allows them to rotate 360 degrees being also optionally secured from rotation by a handwheel lock (11g). A single position switch (11h), located in the top edge of upper support arm (11e) as best illustrated in FIG. 1, allows remote operation of the electro-mechanical servo (10a). This switch is connected to the servo by means of shielded wiring as shown in FIG. 1. Electrical service for various Ophthalmic instruments is provided by a modular receptacle (115) which protrudes through the lower edge of upper support arm (11e) near its free end and, terminates with a plug (11i) at base (1).

In use, the Ophthalmic instrument stand may be placed forward and diagonally from the patient chair instead of directly to the side owing to its relatively low relatively low profile and superior reach of its instrument support are. In a position diagonal to the patient chair, access to the patient is possible in a 360 degree field. This orientation also allows for the examination of wheelchair patients without removing them to the patient in a generally perpendicular manner which reduces the risk of trauma to the legs of patients in the event of an accidental descent of the instrument platform. Further, the overall range of motion needed on behalf of the examiner is reduced by the closer proximity of the stand to the examiner than is possible in prior stands. The generally lower profile of the stand, due to horizontal distribution of weight over pulleys, also facilitates the examination of patients in wheelchairs which removes the need of placing such patients in the patient chair and, removing the risks inherent in such maneuvers to both patient and examiner.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited no by this detailed description, but rather by the claims appended here.

What is claimed is:

1. A low profile ophthalmic instrument support stand comprising:

a free standing counter weighted support base; comprising a roller frame and counter weight suspended over two sets of pulleys and guided by two sets of vertical members of equal height attached to the base at the bottom and to a frame at the top, an electro-mechanical locking mechanism preventing only downward vertical motion of the roller frame, a support arm assembly; comprising a lower support being external to the frame, lower support arm, upper support arm, and receptacle for insertion of the shafts of various ophthalmic instrument platforms, a switch for remote operation of said locking device, a modular receptacle providing providing electrical service to ophthalmic instruments.

2. A device as claimed in claim 1 wherein said counter weight and roller frame are oriented along a single axis which allows the device to balance said lower and upper support arms without the need for attachment of said device to a stabilizing entity.

3. A device as claimed in claims 1 or 2 wherein the use of said roller frame and pulleys enable a smooth and even distribution of loads placed on said lower and upper support arm throughout its entire range of movement.

* * * * *